United States Patent
Boeck et al.

(10) Patent No.: US 8,207,366 B2
(45) Date of Patent: Jun. 26, 2012

(54) METHOD FOR PRODUCING ALKYL CHLOROSILANES FROM THE RESIDUES OF THE DIRECT SYNTHESIS OF ALKYL CHLOROSILANES

(75) Inventors: Manfred Boeck, Burghausen (DE); Paul Fuchs, Schalchen (AT); Konrad Mautner, Riesa (DE)

(73) Assignee: Wacker Chemie AG, Munich (DE)

( * ) Notice: Subject to any disclaimer, the term of this patent is extended or adjusted under 35 U.S.C. 154(b) by 5 days.

(21) Appl. No.: 12/865,664

(22) PCT Filed: Feb. 16, 2009

(86) PCT No.: PCT/EP2009/051771
§ 371 (c)(1), (2), (4) Date: Jul. 30, 2010

(87) PCT Pub. No.: WO2009/106447
PCT Pub. Date: Sep. 3, 2009

(65) Prior Publication Data
US 2011/0009659 A1 Jan. 13, 2011

(30) Foreign Application Priority Data

Feb. 26, 2008 (DE) .......................... 10 2008 000 410

(51) Int. Cl.
*C07F 7/12* (2006.01)
(52) U.S. Cl. ......... 556/468; 556/465; 556/466; 556/467
(58) Field of Classification Search ....................... None
See application file for complete search history.

(56) References Cited

U.S. PATENT DOCUMENTS

| | | | |
|---|---|---|---|
| 2,598,435 A | 5/1952 | Mohler | |
| 2,681,355 A | 6/1954 | Barry | |
| 5,877,337 A | 3/1999 | Mautner | |
| 6,344,578 B1 | 2/2002 | Mautner | |
| 2005/0113592 A1 | 5/2005 | Wagner | |

FOREIGN PATENT DOCUMENTS

| | | |
|---|---|---|
| DE | 19711693 A1 | 9/1998 |
| DE | 10039172 C1 | 9/2001 |
| EP | 1505070 A1 | 2/2005 |

*Primary Examiner* — Yevegeny Valenrod
(74) *Attorney, Agent, or Firm* — Brooks Kushman P.C.

(57) ABSTRACT

High boiling residue from the direct synthesis of alkylchlorosilanes are converted in large part to monosilanes by heating the residue by passage of alternating current in a pressurized reactor.

10 Claims, No Drawings

METHOD FOR PRODUCING ALKYL CHLOROSILANES FROM THE RESIDUES OF THE DIRECT SYNTHESIS OF ALKYL CHLOROSILANES

CROSS-REFERENCE TO RELATED APPLICATION

This application is the U.S. national phase of PCT Appln. No. PCT/EP2009/051771 filed Feb. 16, 2009 which claims priority to German application DE 10 2008 000 410.3 filed Feb. 26, 2008.

BACKGROUND OF THE INVENTION

1. Field of the Invention

The invention relates to a process for producing alkylchlorosilanes from the residues from the direct synthesis of alkylchlorosilanes via heating by alternating current.

2. Description of the Related Art

When metallic silicon and alkyl chlorides RCl, where R is an alkyl moiety, are used in the direct synthesis of alkylchlorosilanes of the general formula $R_aH_bSiCl_{4-a-b}$ in which a is 1, 2, 3, or 4 and b is 0, 1, or 2, the by products comprise oligosilanes, carbosilanes, siloxanes, and high-boiling-point cracking products. The residues also comprise solids derived from the direct synthesis process which are very fine and are not retained by cyclones and filters. These solids are composed of silicon, metals, and compounds of these, metal silicides, and carbon black.

Oligosilanes make up the main part of the residues, and in particular the disilanes of the general formula $R_cCl_{6-c}Si_2$, in which c is from 0 to 6. However, silane compounds having more than 2 Si—Si bonds can also be present, examples being trisilanes or silamethylenes. In all these formulae, silicon is tetravalent.

U.S. Pat. No. 2,598,435 describes a process in which methylchloromonosilanes are obtained from residues from the direct synthesis of methylchlorosilanes which comprise methylhalopolysilanes, at temperatures of from 250 to 800° C.

A wide variety of specifications, e.g. EP 1505070 and publications cited therein, describe processes in which residues from the direct synthesis of alkylchlorosilanes can be cleaved to give alkylchloromonosilanes, using additions of HCl and/or $H_2$ and sometimes using complex catalyst systems. U.S. Pat. No. 2,681,355 describes a continuous process in which residues from the direct synthesis of methylchlorosilanes are reacted in an externally heated tube with HCl at temperatures of from 400 to 900° C. to form monomeric silanes, without catalysis and by a purely thermal route. Large amounts of by products are formed here, examples being carbosilanes and polymers, and also solids, because of carbonization of the residues on hot reactor walls.

DE 19711693 describes a continuous process in which alkylchlorosilanes are produced from the residues from the direct synthesis of alkylchlorosilanes, which comprise liquid constituents with a boiling point >70° C. and solids, using HCl at from 300 to 800° C. in a tubular reactor with rotatable internals. The rotatable internals are needed for scraping to remove caked material produced by carbonization on the reactor walls.

SUMMARY OF THE INVENTION

It was an object to provide a process which can produce alkylchlorosilanes from the residues from the direct synthesis of alkylchlorosilanes and which provides a high yield of alkylchlorosilanes purely via thermal treatment and without further additives, e.g. hydrogen chloride, hydrogen, or catalysts, and which at the same time inhibits carbonization of the residues and formation of deposits on hot reactor walls. These and other objects are achieved by heating the residue in a pressurized reactor by passage of an alternating electric current.

DETAILED DESCRIPTION OF THE PREFERRED EMBODIMENTS

The invention thus provides a process for producing alkylchlorosilanes from the residues from the direct synthesis of alkylchlorosilanes, which comprise liquid constituents with a boiling point of at least 70° C. at 1013 hPa and further constituents, including metals and compounds thereof, in which the reaction mixture is heated in a pressurized reactor to a reaction temperature of from 200 to 500° C. via passage of alternating current.

The process uses residues from the direct synthesis of alkylchlorosilanes to provide useful monosilanes. It is preferable here that relatively high-molecular-weight constituents of the residues are cleaved to give monosilanes. The process preferably requires no use of catalysts and no use of further starting materials. Deposits of solids on the reactor walls are very substantially avoided.

Methylchlorosilanes of the general formula $Me_aH_bSiCl_{4-a-b}$ are preferably produced, in which Me is a methyl moiety, a is 1, 2, or 3, and b is 0 or 1.

The residues from the direct synthesis consist in essence of volatile constituents with a boiling point of at least 70° C., in particular at least 100° C., at 1013 hPa, and metals or compounds of these, in dissolved or finely suspended form. In particular, the residues comprise metals from the group of Al, Cu, Zn, Sn, Fe, Ti, and/or compounds of these. The residues can also comprise further solids, e.g. silicon and carbon black. The residue mostly comprises disilanes.

The residues are introduced batchwise or continuously into a pressurized reactor and heated to the temperature required for reaction via passage of alternating current.

The reactor is preferably operated at at least 250° C. and with preference at at most 350° C.

The pressure is preferably at least 20 bar, more preferably at least 30 bar, and preferably at most 100 bar, in particular at most 80 bar.

The reaction product is preferably condensed, and if appropriate freed from solids, and can be returned to the alkylchlorosilane mixture produced in the direct synthesis process, or else can be separately isolated to give pure substances.

EXAMPLE

Unless otherwise stated, all of the amounts and percentages stated are based on weight. Me means a methyl moiety.

A high-boiling-point residue from the direct synthesis of methylchlorosilanes was used and according to GC was composed of:
54% of disilanes (mixture of 1,1,1,2,2,2-hexamethyl-disilane, 1-chloropentamethyldisilane, 1,1-dichloro-tetramethyldisilane, 1,2-dichlorotetramethyldisilane, 1,1,2-trichlorotrimethyldisilane, and 1,1,2,2-tetrachlorodimethyldisilane),
9% of trisilanes of the general formula
$Cl_aMe_{3-a}Si(Cl_bMe_{2-b})SiSiCl_cMe_{3-c}$, where each of a and c is from 0 to 3, and b is from 0 to 2, 7% of silamethylenes (carbosilanes) of the general formula $Cl_aMe_{3-a}SiCH_2SiMe_{3-b}Cl_b$, where each of a and b is from 0 to 3, 2% of metals and metal compounds (in particular Al, Zn, Sn, Fe, Ti), 2% of alkylchlorosilanes, and also 26% of unidentified compounds, each at low concentration.

The high-boiling-point residue was fed in liquid form into an autoclave of volume 0.92 l. The reaction mixture was heated to 270° C. via passage of alternating current and kept at this temperature for 180 min.

The autoclave was cooled to ambient temperature. The product mixture was removed and analyzed by GC:

51.7% of methylchlorosilanes, of which 40.4% of dichlorodimethylsilane, 7.2% of trichloromethylsilane, 2.5% of chlorotrimethylsilane, 1.4% of dichloromethylsilane, 0.5% of uncleaved disilanes, 6.8% of silamethylenes, 41% of unidentified compounds.

There was only very little solid deposited on the wall of the reactor and on the base of the reactor. The solid was in the form of fine particulates and could easily be removed mechanically.

What is claimed is:

1. A process for producing alkylchlorosilanes from a reaction mixture comprising residues from the direct synthesis of alkylchlorosilanes which comprise liquids with a boiling point of at least 70° C. at 1013 hPa and further constituents comprising metals and metal compounds, comprising heating the reaction mixture in a pressurized reactor to a reaction temperature of from 200 to 500° C. via passage of alternating electrical current through the liquid reaction mixture.

2. The process of claim 1, wherein further constituents in the reaction mixture comprises metal compounds.

3. The process of claim 1, wherein methylchlorosilanes of the formula $Me_aH_bSiCl_{4-a-b}$ are produced, in which Me is a methyl moiety, a is 1, 2, or 3, and b is 0 or 1.

4. The process of claim 1, in which disilanes are present in the residue.

5. The process of claim 1, in which no further starting materials or catalysts are added.

6. The process of claim 1, which is conducted at a pressure of from 20 to 100 bar.

7. The process of claim 1, wherein no HCl and no $H_2$ are added.

8. The process of claim 1, which takes place at a temperature of from 250° C. to 350° C. and at a pressure of from 30 bar to 80 bar.

9. The process of claim 1, further comprising removing a product from the reactor and isolating a pure monosilane from the product.

10. The process of claim 1, further comprising separating a product from the reactor, and adding at least a portion thereof to alkylchlorosilanes produced in a direct synthesis reaction.

* * * * *